US012559374B2

(12) United States Patent
Iakimov

(10) Patent No.: US 12,559,374 B2
(45) Date of Patent: Feb. 24, 2026

(54) PROCESS FOR PRODUCING GRAPHENE DOPED WITH NITROGEN AND SULFUR

(71) Applicant: SEA FURTHER S.À. R.L., mONACO (MC)

(72) Inventor: Valentino Iakimov, Messina (IT)

(73) Assignee: SEA FURTHER S.À R.L., Monaco (MC)

( * ) Notice: Subject to any disclaimer, the term of this patent is extended or adjusted under 35 U.S.C. 154(b) by 851 days.

(21) Appl. No.: 17/762,640

(22) PCT Filed: Sep. 23, 2020

(86) PCT No.: PCT/IB2020/058879
§ 371 (c)(1),
(2) Date: Mar. 22, 2022

(87) PCT Pub. No.: WO2021/059152
PCT Pub. Date: Apr. 1, 2021

(65) Prior Publication Data
US 2022/0348468 A1 Nov. 3, 2022

(30) Foreign Application Priority Data

Sep. 26, 2019 (IT) ........................ 102019000017291

(51) Int. Cl.
| | |
|---|---|
| *C01B 32/194* | (2017.01) |
| *C01B 32/198* | (2017.01) |
| *C12M 1/00* | (2006.01) |
| *C12M 1/34* | (2006.01) |
| *C12P 3/00* | (2006.01) |

(52) U.S. Cl.
CPC .......... *C01B 32/194* (2017.08); *C01B 32/198* (2017.08); *C12M 23/40* (2013.01); *C12M 23/58* (2013.01); *C12M 41/00* (2013.01); *C12P 3/00* (2013.01); *C01B 2204/22* (2013.01); *C01P 2002/52* (2013.01); *C01P 2002/82* (2013.01); *C01P 2002/85* (2013.01)

(58) Field of Classification Search
None
See application file for complete search history.

(56) References Cited

FOREIGN PATENT DOCUMENTS

WO WO-2021059152 A1 * 4/2021 ........... C01B 32/182

OTHER PUBLICATIONS

Chen et al., "One-pot fabrication of nitrogen and sulfur dual-doped graphene/sulfur cathode via microwave assisted method for long cycle-life lithium-sulfur batteries," Journal of Alloys and Compounds, 2018, vol. 746, pp. 116-124.
Miao et al., "Plasma-Assisted Simultaneous Reduction and Nitrogen/Sulfur Codoping of Graphene Oxide for High-Performance Supercapacitors," ACS Sustainable Chemistry & Engineering, 2019, vol. 7, pp. 7597-7608.
Guo et al., "One-Pot Microbial Method to Synthesize Dual-Doped Graphene and Its use as High-Performance Electrocatalyst," Scientific Reports, Dec. 16, 2013, vol. 3, No. 3499, pp. 1-6.
Tian et al., "Metal-free N, S co-doped graphene for efficient and durable nitrogen reduction reaction," Journal of Materials Science, 2019, vol. 54, No. 12, pp. 9088-9097.
Akhavan, O., "Bacteriorhodopsin as a superior substitute for hydrazine in chemical reduction of single-layer graphene oxide sheets," Carbon 81, 2015, pp. 158-166.
Nov. 19, 2020 International Search Report issued in International Patent Application No. PCT/IB2020/058879.
Nov. 19, 2020 Written Opinion of the International Searching Authority issued in International Patent Application No. PCT/IB2020/058879.

* cited by examiner

*Primary Examiner* — Hope A Robinson
(74) *Attorney, Agent, or Firm* — Oliff PLC

(57) ABSTRACT

A process to produce graphene dual doped with nitrogen and sulfur atoms through a reduction of graphene oxide by microorganisms. Also, graphene dual doped with nitrogen and sulfur atoms obtainable by this process, and the use of the doped graphene to produce e.g. electronic components or water purification equipment. The process is eco-sustainable and economic with the additional advantage of providing a product with significantly improved performance compared to known products.

10 Claims, 7 Drawing Sheets

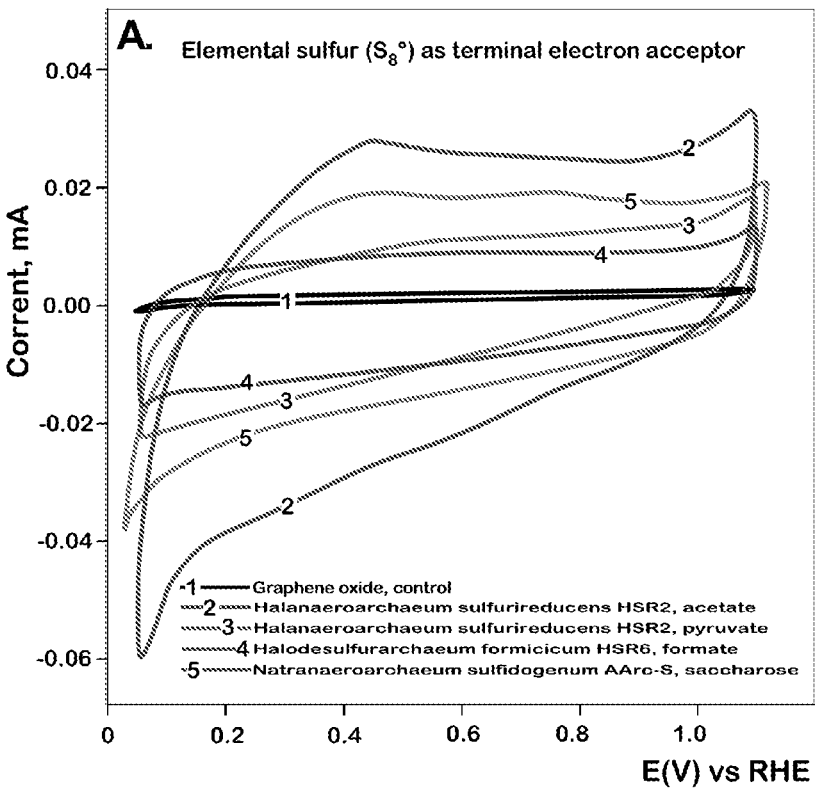

A. Elemental sulfur (S₈°) as terminal electron acceptor

-1 ——— Graphene oxide, control
2 ~~~ Halanaeroarchaeum sulfurireducens HSR2, acetate
3 ~~~ Halanaeroarchaeum sulfurireducens HSR2, pyruvate
4 ~~~ Halodesulfurarchaeum formicicum HSR6, formate
5 ~~~ Natranaeroarchaeum sulfidogenum AArc-S, saccharose E(V) vs RHE

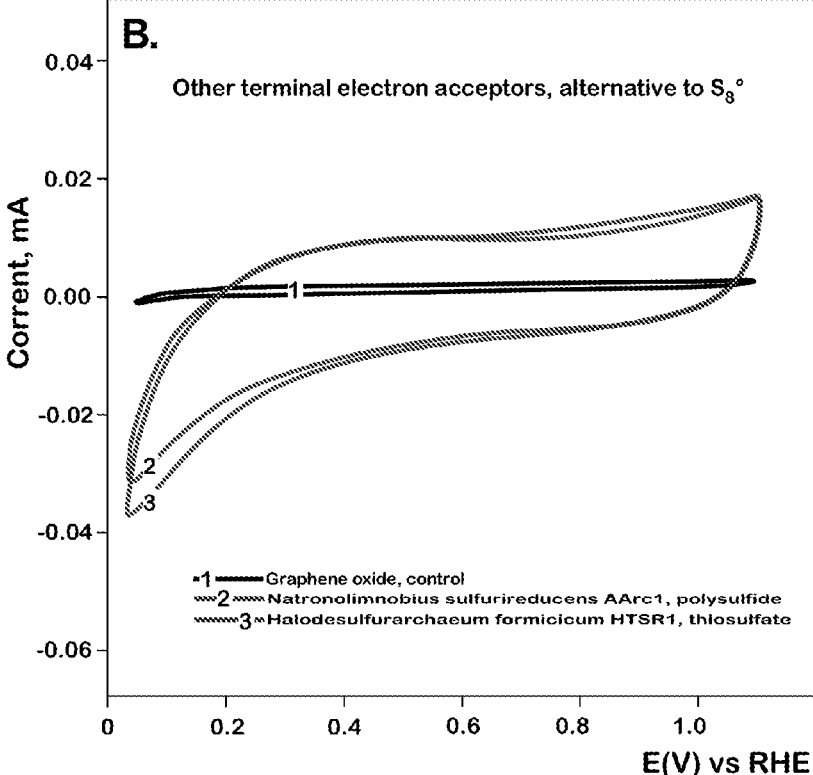

B. Other terminal electron acceptors, alternative to S₈°

-1 ——— Graphene oxide, control
2 ~~~ Natronolimnobius sulfurireducens AArc1, polysulfide
3 ~~~ Halodesulfurarchaeum formicicum HTSR1, thiosulfate E(V) vs RHE

FIG. 4

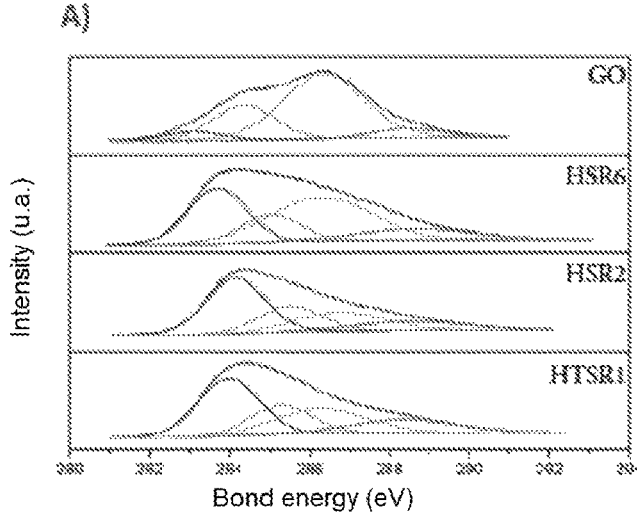
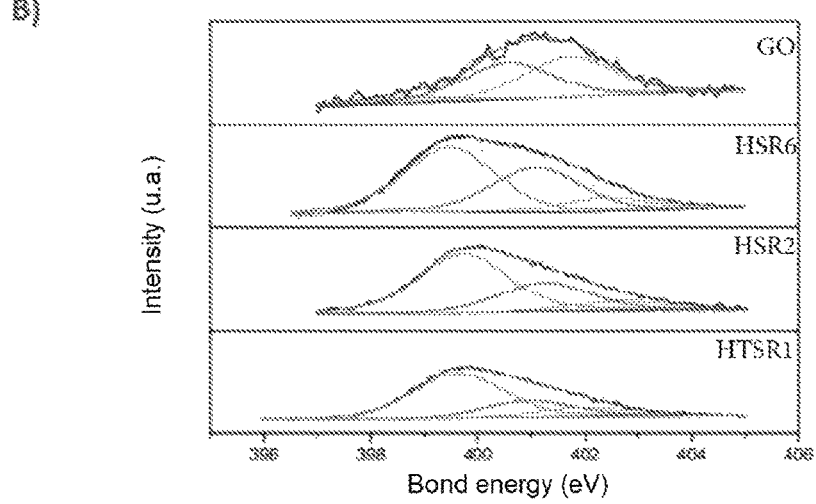
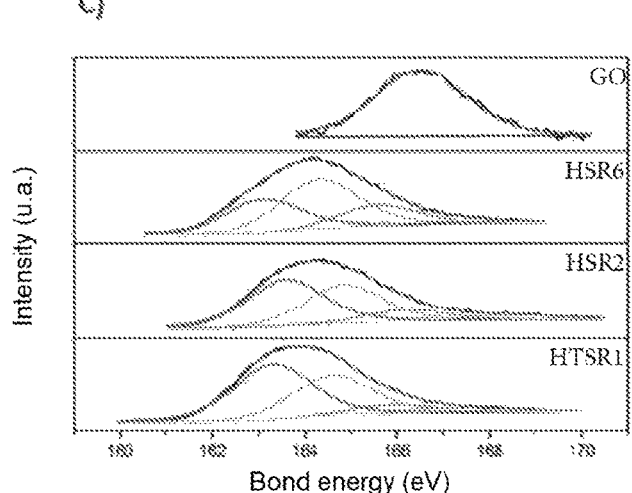
FIG. 5

Analysis of the chemical form of S element in the graphene sample modified by AARC-S cultured with thiosulfite

PROCESS FOR PRODUCING GRAPHENE DOPED WITH NITROGEN AND SULFUR

This application is a national phase entry of PCT/IB2020/058879 filed Sep. 23, 2020 and claims priority to IT 102019000017291 filed Sep. 26, 2019.

TECHNICAL FIELD OF INVENTION

This invention refers to a process to produce a graphene doped with nitrogen and sulfur atoms through a reduction of graphene oxide by microorganisms. In addition, this invention relates to nitrogen- and sulfur-doped graphene obtainable by this process, and to the use of graphene so doped to produce e.g. electronic components or water purification devices. In particular, the process is eco-sustainable and economical with the additional advantage of providing a product with significantly improved performance compared to known products.

STATE OF THE ART

Graphene is known to be a monatomic layer of carbon atoms. It has the mechanical strength of diamond and the flexibility of plastic. Its discovery in practice, attributable to the two physicists Andrej Gejm and Konstantin Novosslov, has opened new paths in nanotechnology. Specifically, graphene is extremely stable, providing exceptional mechanical, thermal, optical, and chemical characteristics, as well as improved electrical characteristics, as demonstrated experimentally through a great amount of research conducted over the last decade.

As suggested by the name ("ene" termination), the carbon atoms are hybridized in the $sp^2$ form, and thus arranged to form hexagons with 120° angles disposed in a pattern with high crystalline characteristics. Therefore, being a two-dimensional crystalline material, graphene provides unique and adjustable physical properties, i.e. controllable, making it possible to manufacture various devices with different functionalities including sensors, transistors, memories, filtering systems and the like that can be used in many fields such as electronics, biology, biotechnology, energy and others. The promising characteristics of graphene in these areas require the definition of large-scale production processes to anticipate the increase in demand. Moreover, due to the graphene's easily modifiable structure, its extremely interesting physical-chemical properties and its abundance in nature, this material has been associated with a "malleable clay".

As known in the state of the art, to allow the use of this material for different devices in many fields it is necessary to subject graphene to a doping process suitable to improve its properties with respect to unmodified graphene. In fact, doping of graphene with heteroatoms is an effective way to improve its properties, preferably to improve its electrical properties. Therefore, presently, the most of the researches in this field are focused towards the modification of the graphene properties through doping.

Specifically, the insertion of different atoms such as Nitrogen (N) and Sulfur (S) in graphene oxide causes the interruption of the $sp^2$ carbon atoms pattern, affecting the chemical and physical properties of the graphene, allowing the properties to be adjusted according to the degree and type of doping. Theoretical studies indicated that the doping of graphene with Nitrogen (N) and Sulfur (S) advantageously modifies its properties, preferably those electrochemical, producing the so-called "N,S-dual doped graphene" (N,S-DDG), that as will be demonstrated further can for instance be transformed in a catalyst for oxygen reduction reaction.

Currently, the typically used and most effective process for graphene doping is based on the deposition of chemical substances evaporated on the graphene surface in a reactor heated to 800° C. (technique of Chemical Vapor Deposition, CVD). Specifically, to produce N,S-dual doped graphene oxide (N,S-DDG), graphene oxide (GO) is used as the starting material and is doped with chemicals such as methane ($CH_4$), ammonia ($NH_3$) and sulfuric acid ($H_2SO_4$). Without being bound to any theory, at high temperature (800° C.) some covalent bonds are broken, such as those with the nitrogen atom in ammonia, the sulfur atom in sulfuric acid and the hydrogen atoms associated with each of doping substances. Then, under reactor conditions, the resulting unstable molecules, such as amide ion ($NH_2^-$) and sulfate ion ($SO_4^{2-}$), interact with the graphene covalent bonds, also weakened by high temperature, modifying its chemical composition and transforming it into N,S-dual doped graphene (N,S-DDG).

In a process as above, polluting chemicals for the environment and toxic for human beings are used, namely methane ($CH_4$), ammonia ($NH_3$) and sulfuric acid ($H_2SO_4$). The temperatures of the process are very high and it is necessary to foreseen a suitable plant adapted to sustain such conditions. Further, the security risk for the operators is very high due to the methane being inflammable in presence of oxygen (potentially released by graphene oxide or accidentally introduced into the plant).

The final purification treatment of N,S-dual doped graphene (N,S-DDG) includes the removal of toxic residues of the used substances of the preceding steps, namely ammonium ($NH_3^+$) and sulphate ($SO_4^{2-}$) ions. Typically, this purification step of the N,S-dual doped graphene (N,S-DDG) includes a dissolution of said residues by rinsing with hydrochloric acid (HCl). Therefore, the process comprises a further pollutant and toxic substance, i.e. just hydrochloric acid (HCl), which is added to the list of the substances, above described, necessary to perform the process and which can also affect graphene properties such as robustness.

As an alternative to the previously exposed procedure, the use of micro-organisms has been proposed to allow, in certain phases, less critical experimental conditions than those described above.

The scientific publication "*One-Pot Microbial Method to Synthesize Dual-Doped Graphene and Its Use as High-Performance Electrocatalyst*, Guo et al., 16 Dec. 2013", which is incorporated herein as a reference, describes a process for the reduction of graphene oxide (GO) by microbial respiration of sulphate-reducing bacteria (SRB).

Specifically, this document describes a procedure for the preparation of N,S-dual doped graphene (N,S-DDG) by reduction of graphene oxide (GO), through microbial respiration of sulphate-reducing bacteria (SRB) at a temperature of 37° C., in order to obtain the desired doping with N and S atoms.

It is well known that during anaerobic respiration the sulfate-reducing bacteria (SRB) predominantly use sulfate ($SO_4^{2-}$) as a terminal electron acceptor. Since graphene oxide (GO) apparently has demonstrated electron acceptor properties, it is possible to achieve the reduction of graphene oxide (GO) during the SRB respiration process.

It should be noted that the SRB bacteria used in this procedure derived from moist oily soils of Shengli (China) and were grown in the API-RP38 culture medium consisting of (per liter of ultrapure water): 4.0 mL of sodium lactate, 1.0 g of yeast extract, 0.2 g of magnesium sulphate ($MgSO_4 \cdot 7H_2O$), 0.1 of vitamin C (Vc), 0.01 g of potassium diphosphate ($K_2HPO_4$) and 10 g of sodium chloride (NaCl). The pH is adjusted to 7.0-7.2 with 1 M sodium hydroxide (NaOH). The final solution is sterilized in an autoclave at 121° C. for 20 min, cooled to room temperature and added with 0.2 g of $FeSO_4 \cdot (NH_4)_2SO_4 \cdot 6H_2O$ sterilized with ultraviolet light.

Graphene oxide (GO) reduction was achieved by mixing 100 mL of a GO solution (0.1 mg·mL$^{-1}$) with 10 mL of SRB culture and 30 mL of fresh culture medium. The mixture was incubated under anaerobic conditions at 37° C. in an incubator for several days.

The resulting black dispersion was centrifuged (14000 rpm) and washed with an aqueous HCl solution to remove organic matter, cellular debris, and ultrapure water several times. Finally, the resulting solids were dried at 80° C. under vacuum.

As detected by high resolution X-ray photoelectron spectroscopy XPS spectrum for nitrogen, the atomic percentages of doped nitrogen and sulfur were approximately 6.11% and 1.1%, respectively.

Said procedure is surely advantageous because thanks to the use of sulfate-reducing bacteria (SRB) doping conditions are drastically reduced. In particular, the temperatures are much lower, and the reagents are completely environmentally friendly, apart from the final washing phase.

Nevertheless, the performances of N, S-DDG obtained with the aforesaid microbiological process have not proved to be satisfactory. In fact, it has been experimentally observed that the more similar the distribution of N and S on graphene is, the more efficient the doped graphene is, i.e. it appears conductive for the current. In other words, without being bound to theories, it would seem that the ratio in % between N and S must be as close as possible to the value of 1:1 to obtain an excellent substrate from the point of view of electrical conductivity.

Furthermore, SRB are overly sensitive to high amounts of GO. This would significantly limit their use at large scale production, since the insertion of too much high doses of GO, as instead required just for an industrial process, would cause the death of the "doping" bacteriologic culture.

Finally, notwithstanding a detailed physicochemical characterization of the microbiologic-doped graphene oxide, the above publication does not describe in a sufficient clear manner the N, S-DDG synthesis for the skilled person in the art. More specifically, any information concerning the isolation and obtaining of SRBs, as well as the conditions of maintenance/cultivation in the laboratory, are missing. Therefore, this publication does not provide all the information necessary to reproduce the described process, on any scale. It can be only assumed that the authors have isolated a SRB bacterium of the class Deltaproteobacteria, that is the genera of sulfate-reducing bacteria used, without disclosing any species, which could thus be highly variable; likely belonging to *Desulfovibrio, Desulfobacter, Desulfococcus* o *Desulfonema*.

Consequently, there is a need to define a process for the preparation of N, S-dual doped graphene oxide (N,S-DDG) which overcome the problems described above. Specifically, the production process, preferably on a large scale, must employ conditions with low pollution risk, low hazard for the operators, such as low temperatures and minimized use of polluting and toxic products, and at the same time must guarantee a final product possessing high performance in terms of electrical conductivity.

SUMMARY OF THE INVENTION

The technical problem underlying the present invention is therefore to provide a process for the production of graphene doped with nitrogen and sulfur atoms (N,S-DDG) that does not involve the massive use or risk of release of chemicals that are pollutant to the environment and toxic to humans, such as methane ($CH_4$), ammonia ($NH_3$) and sulfuric acid ($H_2SO_4$), and which involves substantially low reaction temperatures.

The above problem is solved by a process to produce graphene dually doped with nitrogen and sulfur atoms (N,S-DDG) which involves a reduction phase of graphene oxide (GO) by means of specially selected microorganisms.

Therefore, a first object of this invention is a process to produce graphene dually doped with nitrogen and sulfur atoms (N,S-DDG) comprising an step of contacting a culture of selected microorganisms with a mixture of graphene oxide (GO).

A second object is a process for the production of graphene dually doped with nitrogen and sulfur atoms (N,S-DDG) wherein the culture medium provides also the necessary elements for the doping of reduced graphene oxide (GO), such as nitrogen (N) and sulfur (S).

A third object is a process for the production of graphene doped with nitrogen and sulfur atoms (N,S-DDG) practically free of non-operative phases, i.e. "in loop" process or a continuous recirculation process that does not require interruption as it takes place in an isolated systems.

A further object is a process that allows the release of unstable active molecules with a high insertion rate into graphene oxide, resulting from products with very low toxicity and very low contamination grade.

A still further object is the use of special microorganisms to produce graphene dually doped with nitrogen and sulfur atoms.

A still further object is a graphene dually doped with nitrogen and sulfur atoms (N,S-DDG) which obtainable by this process whose costs, thus, is low and with a minimized risk on the environment and human health.

A still further object is a simplified production plant specially designed in a simple manner to reduce the costs of producing graphene dually doped with nitrogen and sulfur atoms (N,S-DDG).

A final object is the use of doped graphene according to this invention for the production of electronic and electrochemical components (e.g. fuel cells), analytical systems, purification systems and nanomaterials used as medical, telephone, aeronautical, aerospace, robotics nano-components, eco-sustainable macro-materials as automotive mechanical, aeronautical, aerospace robotics components.

The problems and objects indicated above, and others that will better appear later in the description, are solved and achieved by a process, a plant, particular doping microorganisms, graphene and its use as defined in the attached independent claims.

BRIEF DESCRIPTION OF THE FIGURES

Further characteristics and advantages of the process for the production of graphene dually doped with nitrogen and sulfur atoms (N,S-DDG), according to the present invention, will become apparent in the following description of some preferred embodiments given as a non-limiting example, also with reference to the following figures, wherein:

FIG. 4 represents two comparative graphs of the result between a cyclic voltammetry of graphene oxide (control) and graphene oxide samples doped with N and S, obtained using different haloarchaea species grown on different carbon sources, where elemental sulfur was provided as terminal electron acceptor (graph A), and grown on format, where thiosulfate and polysulfide were provided as electron acceptors (graph B);

FIG. 5 shows three graphs each showing the XPS spectra of three graphene doped samples using a species of microorganism (HSR) grown with three different substrates (PYR, AC, FORM), against non-doped graphene oxide, respectively a) for 1s hybridization of C, b) for 1 s hybridization of N and c) for 2p hybridization of S;

DETAILED DESCRIPTION OF THE INVENTION

Figure 1:
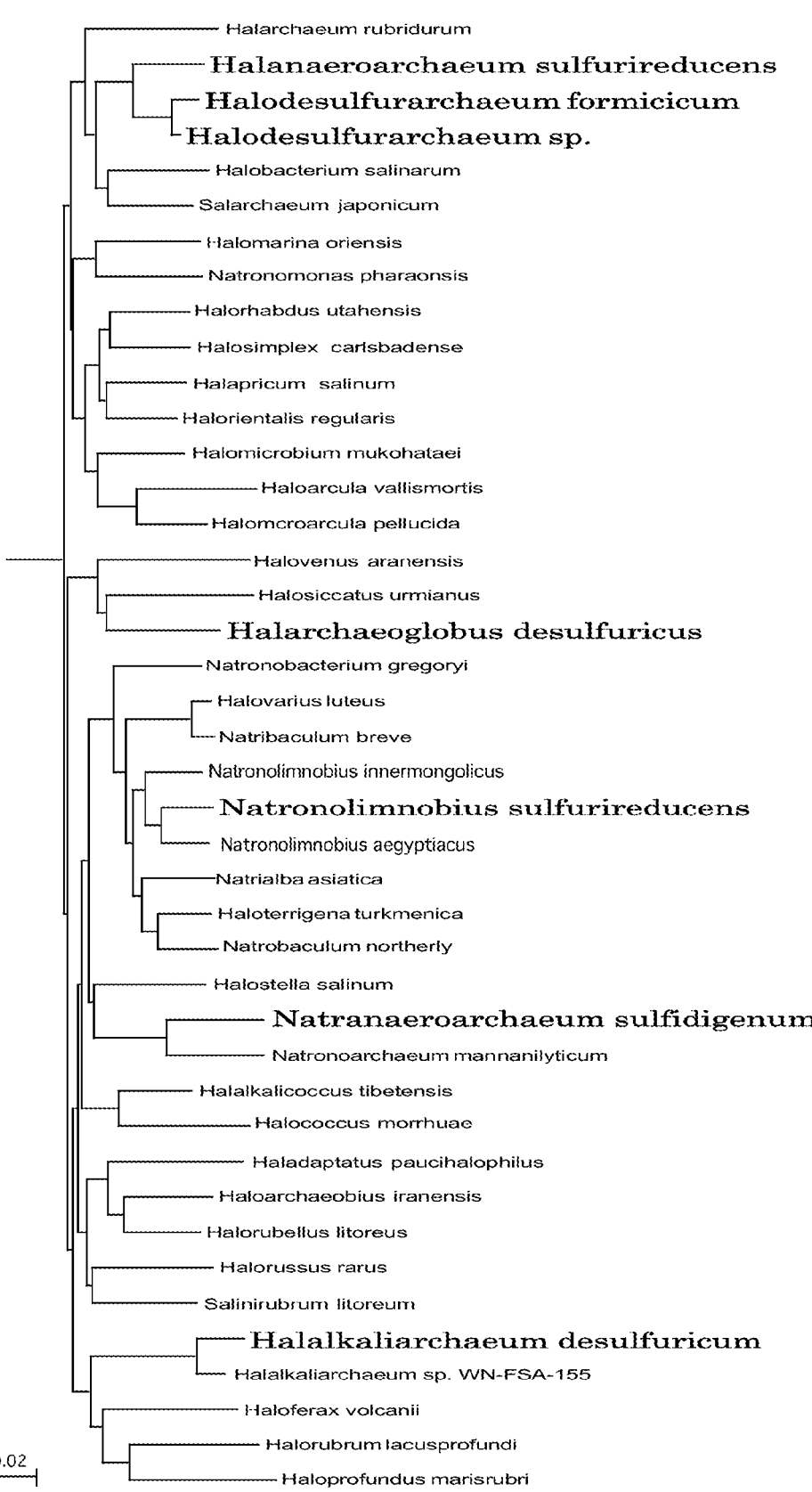
FIG. 1 represents a phylogenetic tree showing the positioning of six new haloarchaea species belonging to the class Halobacteria, the clade Stenosarchaea group, the phylum Euryarchaeota.

This invention essentially refers to a biochemical process of doping graphene oxide (GO) foreseen for the industrial application of nanomaterial. The so-called "doping" is a process, exclusively made possible by the physical proximity between the graphene oxide, the specific microorganisms, and their cultivation medium. In the following description, the term 'doping' and related words means a process of altering the chemical composition of molecule by the insertion of atoms initially absent in its original structure. This process modifies the physicochemical properties of the material subjected to it. In the particular case of the invention "N,S-DDG" means graphene doped with nitrogen (N) and sulfur (S) atoms, i.e. literally, N [nitrogen], S [sulfur]-D [Dual] D [Doped] G [Graphene].

It should be noted that except for the final purification step of the product, no intervention is necessary to carry out the doping.

In addition, generally, the respiratory function of the selected microorganisms allows the release of unstable molecules with a very high insertion rate. The proximity between unstable molecules and the GO then allows the insertion of sulfur (S) and nitrogen (N) atoms into the bi-dimensional structure of graphene oxide $(C_nH_iO_j)$ in a surprisingly efficient way.

As already explained, the physicochemical properties of reduced graphene oxide so doped are nowadays recognized for their versatility in various applications: from the replacement of silicon semiconductors to the operation of innovative water decontamination systems. Therefore, a simple, effective, and economical process is of great interest.

According to the present invention, therefore, the process to produce graphene doped with nitrogen and sulfur atoms (N,S-DDG) comprises the steps of:

providing microorganisms of the Halobacteria class which are strictly anaerobic and sulfite-reducing and capable of living between 20° C. and 50° C. in salinity condition over 200 g·L−1 and at a pH comprised between 7.0 and 10.0;

cultivating said microorganisms in a medium comprising as electronic donor, in an amount up to 100 mmol, Hydrogen (H2), acetate (C2H4O2), formate (CH2O2), glycerol (C3H8O5), glucose (C6H12O6), sucrose (C12H22O11) and other similar sugars, lactate (C3H6O3), short chain fatty acids (C4-C9) and/or pyruvate (C3H4O3), and as electronic acceptor, in an amount up to 50 mmol, any one of sulfur form more oxidized than S2- comprising elemental sulfur (S8°), polysulfide (—S—S6-S—), thiosulfate (S2O32-), dimethylsulfoxide (CH3)2SO, tetrathionate (S4O62-);

contacting a solution of graphene oxide (GO) with said culturing medium containing said microorganisms for a time sufficient to obtain the doping with Nitrogen and Sulfur;

washing the graphene to eliminate both the organic phase and the molecules containing Nitrogen and Sulfur that have not reacted with graphene oxidized.

The step of providing microorganisms is particularly important, since the information of the prior art concerning the use of microorganisms to carry out the biological doping of graphene are not sufficient and clear to provide data on the real efficacy of such a process.

As it described above, the microorganisms till now experimentally used for doping graphene belongs to the kingdom Eubacteria, stem of the "classical" bacteria, sulfate-reducing bacteria (SRB) group, that is chemo-synthetic bacteria oxidizing sulfide acid in Sulfur, Sulfur in sulfurous and sulfuric acid and thiosulfate in sulfate.

Even if taxonomy is continuously rearranged on the basis of the discovery of new species of microorganisms, in any case Eubacteria are unanimously considered radically different from Archaea, to which the class Halobacteria (or Haloarchaea) belong.

Preferably, Halobacteria of the present invention are selected from the genera *Halalkaliarchaeum, Halanaeroarchaeum, Halodesulfurarchaeum, Halarchaeoglobus, Natranaeroarchaeum* and *Natronolimnobius* (FIG. 1) and, more preferably: among the genera *Halalkaliarchaeum* the specie *Halalkaliarcheum desulfuricum*, among the genera *Halanaeroarchaeum* the specie *Halanaeroarchaeum sulfurireducens*; among the genera *Halodesulfurarchaeum* the specie *Halodesulfurarchaeum formicicum*; among the genera *Halarchaeoglobus* the specie *Halarchaeoglobus desulfuricus*; among the genera *Natranaeroarchaeum* the specie *Natranaeroarchaeum sulfidigenum*; among the genera *Natronolimnobius* the specie *Natronolimnobius sulfurireducens*. Using simple organic substances, such as acetate $(C_2H_4O_2)$, format $(CH_2O_2)$, glycerin $(C_3H_8O_5)$, glucose $(C_6H_{12}O_6)$, sucrose $(C_{12}H_{22}O_{11})$ and/or pyruvate $(C_3H_4O_3)$ as the electronic donors, these physiologically exclusive organisms reduce both elemental sulfur $(S_8°)$, polysulfide $(—S—S_6—S—)$, thiosulfate $(S_2O_3{}^{2-})$, dimethyl-sulfoxide $(CH_3)_2SO$, tetrathionate $(S_4O_6{}^{2-})$ and produce $H_2S$ as the end product of their sulfur-dependent respiration.

In particular, the above species *Halalkaliarcheum desulfuricum* and *Natronolimnobius sulfurireducens* are described and characterized respectively with the codes AArc-S and AArc1 in *"Sulfur respiration in a group of facultatively anaerobic natronoarchaea ubiquitous in hypersaline soda lakes"*, *Frontiers in Microbiology, Volume 9, Article* 2359, 2 Oct. 2018, Sorokin et al. The species *Halodesulfurarchaeum formicicum* is described and characterized with the codes HTSR1 and HSR6 in *"Discovery of anaerobic lithoheterotrophic haloarchaea, ubiquitous in hypersaline habitats"*, *The ISME Journal, volume* 11, pages 1245-1260 (2017), Sorokin et al. The species *Halanaeroarchaeum sulfurireducens* is described and characterized with the HSR2 code in *"Elemental sulfur and acetate can support life of a novel strictly anaerobic haloarchaeon"*, *The ISME Journal, volume* 10, pages 240-252 (2016), Sorokin et al. The species *Halarchaeoglobus desulfuricus* is described and characterized with the HSR12 code and has been deposited at the UNIQEM (Culture Collection of Winogradsky Institute of Microbiology) collection center of the Russian Academy of Sciences in Moscow with the identified number $U1000^T$. The species *Natranaeroarchaeum sulfidigenum* is described and characterized with the code AArc-S and has been deposited at the UNIQEM (Culture Collection of Winogradsky Institute of Microbiology) collection center of the Russian Academy of Sciences in Moscow with the identified number $U999^T$.

In addition, the species *Halodesulfurarchaeum formicicum* HTSR1 in that article was deposited at the UNIQEM collection center of the Russian Academy of Sciences in Moscow. Its genome is then available in the GenBank database with access number CP016070. The species *Natronolimnobius sulfurireducens* AArc1 has been deposited at the UNIQEM collection center of the Russian Academy of Sciences in Moscow under the identification number $U932^T$ and at the Japanese Microorganism Collection Centre under the access number JCM $30663^T$. The species *Halodesulfurarchaeum formicicum* HSR6 has been deposited at the same Russian center (UNIQEM) under the number $U983^T$ and at the Japanese center JMC under the number $30662^T$. The species *Halalkaliarchaeum desulfuricum* AArc-S1 was deposited at UNIQEM under the number $U999^T$ and at the JCM center under the number $30664^T$. As stated in aforementioned publications, all these haloarchaea have a kind of sulfur respiration based on sulfur unknown. They are, anyway, ubiquitous in some hypersaline habitats. Using the above described growing culture, archaea strains belonging to the genera *Halanaeroarchaeum, Halodesulfurarchaeum, Halarchaeoglobus, Natranaeroarchaeum* and *Natronolimnobius* were isolated from brine and hypersaline sediment samples collected on volcanic island Stromboli (Aeolian Archipelago, Mediterranean Sea, Italy). These strains were analyzed and showed identical chemical/morphological/genetic characteristics to the strains described in the above-mentioned publications and were therefore indicated with the same codes.

It has been observed that the activity of all the above-mentioned microorganisms ends up with the production up to 10-15 mmol of $H_2S$ in the terminal phase of the respiration process. Furthermore, these microorganisms advantageously have a great resistance against toxicity of GO. In fact, it has been demonstrated that the presence of GO negatively affects the growth and living conditions of SRBs, but not the above-mentioned Halobacteria. In particular, as explained below, to proceed with GO doping it has been used a quantity of 1.0-2.0 $mg \cdot mL^{-1}$, i.e. 10 to 20 times higher than the one which was used by Guo et al. (2013).

Therefore, the use of these particular and selected microorganisms allows for a much more performing doping than the previously described biological process.

The culture medium also allows from one side the growth of the microorganisms and, at the same time, provides the necessary sources of nitrogen and sulfur for doping graphene oxide (GO).

Preferably, said culture medium comprises 240 $g \cdot L^{-1}$ of NaCl, 3 $g \cdot L^{-1}$ of $K_2HPO_4$, 0.5 $g \cdot L^{-1}$ of $NH_4Cl$, 1-5 mM of $MgCl_2 \times 6H_2O$, sterilized and then added with 20-50 $mg \cdot L^{-1}$ of yeast extract, 1 $ml \cdot L^{-1}$ of acidic trace-metal solution, 1 $mL \cdot L^{-1}$ of Se/W alkaline solution and a mixture of vitamins. The final pH is controlled at 7. More preferably, with the species *Halodesulfurarchaeum formicicum* and the species *Halanaeroarchaeum sulfurireducens*, the culture medium also comprises 10 $g \cdot L^{-1}$ of HEPES. In addition, 1 mL of the acidic solution of trace metals preferably comprises the following substances (to one liter of culture medium): HCl 0.01 N (i.e. 10 mmol), 0.6 g $COCl_2 \times 6H_2O$, 30 mg $CuCl_2$, 0.3 g $FeCl_2 \times 4H_2O$, 1.14 g $H_3BO_3$, 4 g $MnCl_2 \times 4H_2O$, 0.5 g $Na_2MoO_4 \times 2H_2O$, 0.3 g $NiCl_2 \times 6H_2O$ and finally 0.42 g $ZnCl_2$.

Preferably, the vitamin mixture comprises, for 1 liter of distilled water: 1 mg of vitamins B12, 20 mg of biotin, 20 mg of folic acid, 50 mg of nicotinic acid, 50 mg of p-aminobenzoic acid, 50 mg of calcium pantothenate, 100 mg of pyridoxine×HCl, 50 mg of riboflavin, 50 mg of thiamine and 50 mg of thionic acid.

The Se/W alkaline solution preferably consists of the following substances (for one liter of 0.01 N [i.e. 10 mmol] NaOH): 2 mg $Na_2SeO_3$ and 4 mg $Na_2WO_4 \times 1.5H_2O$.

The pH of the medium can also be adjusted to specific requirements, e.g. to 7.0 by adding 1 M KOH.

According to an embodiment of the invention, the culture medium consists in the mixture of two culture media: the first comprising 240 $g \cdot L^{-1}$ of NaCl, 5 $g \cdot L^{-1}$ of KCl, 2 $g \cdot L^{-1}$ of $K_2HPO_4$; 0.5 $g \cdot L^{-1}$ of $NH_4Cl$, the second 190 $g \cdot L^{-1}$ of $Na_2CO_3$, 30 $g \cdot L^{-1}$ of $NaHCO_3$, 16 $g \cdot L^{-1}$ of NaCl, 5.0 $g \cdot L^{-1}$ of KCl, 8 mM of $NH_4Cl$, 1.0 $g \cdot L^{-1}$ of $K_2HPO_4$. Both the media are supplemented with 1 mM of $MgCl_2 \times 6H_2O$. As before, after sterilization, 20-50 $mg \cdot L^{-1}$ of yeast extract, 1 $ml \cdot L^{-1}$ of the above mentioned acid trace metal solution, 1 $mL \cdot L^{-1}$ of the above mentioned Se/W alkaline solution and the above mentioned vitamin mixture are added. The final pH is adjusted to 7. More preferably, with the species *Halodesulfurarchaeum formicicum* and the species *Halanaeroarchaeum sulfurireducens*, the above medium also includes 10 $g \cdot L^{-1}$ of HEPES.

According to a further embodiment, the culture medium used for growing *Halalkaliarchaeum desulfuricum* is preferably obtained by mixing the first and the second medium in a ratio of 1:1 in order to obtain a final pH of 9.6, while the culture medium for *Natronolimnobius sulfurireducens* is formed by mixing the first and second culture medium in a ratio of 3:1 in order to obtain a final pH of 9.3.

In general, the microorganisms of the invention are kept in their culture medium during growth under static conditions, i.e. without agitation.

The step of contacting graphene oxide (GO) with the cell culture is preferably performed by adding graphene oxide (in solid phase, as a powder) directly in the cell growth culture, at concentrations less than or equal to 2 $mg \cdot mL^{-1}$, for a period between 10 days and 30 days at a temperature between 20° C. and 50° C., with or without stirring.

This phase is carried out in an isolated doping chamber or container in which the empty space, i.e. not filled by the cell culture containing graphene oxide, is saturated with inert gas such as nitrogen or argon.

At the end of the contact phase of the microorganism with graphene oxide, i.e. the doping phase, the washing phase preferably includes a separation phase of the organic matter from doped graphene oxide, e.g. by centrifugation and/or filtration. More preferably, this phase includes centrifugation at 2,000-6,000×g for 2-10 minutes to separate the doped graphene, followed by washing the graphene with an isotonic solution (240 g·L$^{-1}$ of NaCl) and two successive washing steps with tap or distilled water, followed by a filtration phase on Whatman™ qualitative filter paper, Grade 1 with porosity between 5 and 20 μm to retain the doped graphene.

After the filtration phase, a further washing step may be applied, rinsing the material retained on the filter, e.g. by means of Milli-Q™ water. The rinsing can be repeated two or more times preferably under agitation in a container or wash chamber. Finally, the treated material is dried for 2-6 hours at 40°-80° C. in a conventional oven.

Conveniently, neither organic solvents nor acidic substances are required in any of the above-mentioned processing or washing steps of the N,S-DDG product.

A second object of this invention is the use of strictly anaerobic and sulfur-reducing microorganisms of the class Halobacteria for reduction and simultaneously doping of graphene oxide with sulfur and nitrogen. Such microorganisms can live between 20° C. and 50° C. in salinity conditions above 200 g·L$^{-1}$ and a pH between 6.5 and 10.0. Preferably, the microorganisms are those described above.

Figure 2:
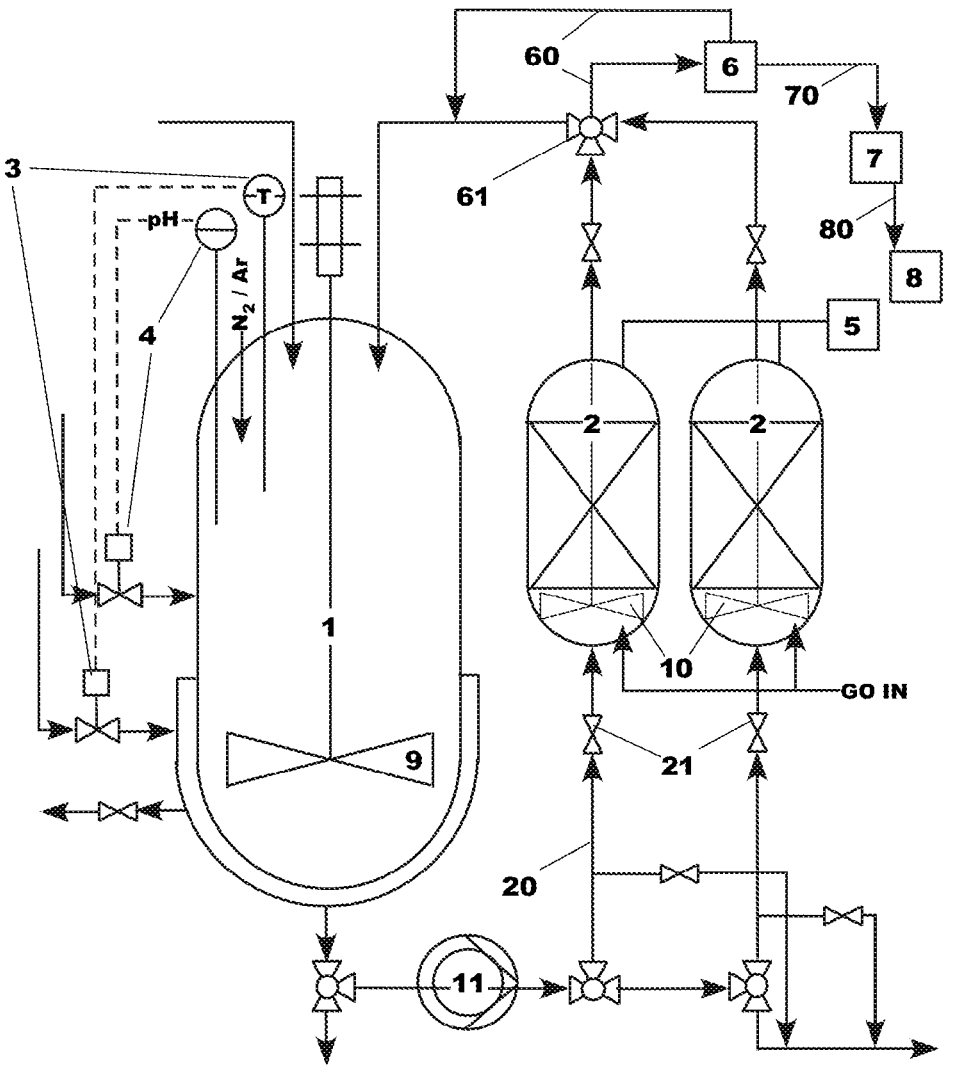
FIG. 2 represents a general scheme of industrial process to produce grapheme, doped with nitrogen and sulfur atoms according to the present invention.

According to a third object of the invention, as shown in FIG. 2, the process described above can be carried out in a plant for the production of graphene dually doped with nitrogen and sulfur comprising a first storage and maintaining/growth container 1 of the graphene oxide reducing micro-organisms described above, at least a second container (doping chamber of graphene oxide) 2 for mixing the mentioned microorganisms with graphene oxide (GO), which second container is hydraulically connected to the first container, a conditioning means 3 of the first container, a pH control and adjustment means 4 connected to the first container, a temperature control and an adjustment means 5 of the second container, a separation/washing device 6,7 of the doped graphene oxide and a drying means 8 of the doped and washed graphene.

Preferably, the first container 1 comprises stirring means 9 for the microorganism culture medium consisting, for example, of a paddle stirrer driven in rotation by a suitable motor with adjustable speed and controllable by conventional devices (not shown in FIG. 2). Containers with such functions are, for example, those sold by Eppendorf under the trade name New Brunswick® BioFlo Fermenters & CelliGen® Bioreactors.

Conditioning means 3 of the first container preferably include a thermometer capable of detecting the temperature inside the container and sending a signal to a conventional control unit which detects this signal and processes it in order to control the circulation of a heating fluid on the outer wall of the container at the set temperature for the maintenance of microorganisms. Instead of the heating fluid, it is possible to use electrical elements such as coils. In any case, the heating devices are completely conventional and are used, for example, in the above-mentioned Eppendorf product.

The control and adjusting means 4 for pH comprise fully conventional sensors or pH-meter connected to a control unit that receives a representative signal of the pH inside the container 1 and sends a signal to any peristaltic pump (not shown) for the release of an acid (such as HCl) or basic (such as KOH) substance in order to maintain the pH at the desired conditions for the prosperity of the microorganisms.

The means for temperature control and regulation in the second container 5 may also be identical to the conditioning ones described with reference to the first container 3. The second container may likewise comprises a stirring device 10 identical to those described above.

Separation/washing means 6,7 for removal of the organic phase of the doped graphene comprises centrifuges and/or Whatman™ qualitative filter paper, Grade 1 with porosity between 5 and 20 μm. Bench centrifuges are suggested, such as the Eppendorf™ 5804R centrifuge. Preferably, separation/washing media are vacuum filters comprising a funnel mounted on the mouth of a flask and equipped with a filter, the flask being connected to a vacuum pump. Such systems are for example sold by Membrane Solution LLC under the trade name BIO-PURE® Vacuum Filters, SIGMA-ALDRICH®.

Further separation/washing means may be e.g. glass solvent systems, i.e. hard glass compound filtration systems designed to isolate bodies (microorganisms, precipitates, and similar particles) from a liquid suspension.

Therefore, these means can be identified either as systems for simple separation, such as centrifuges, or as systems for washing, which also include a separation through filtration.

Drying means 8 comprises a static oven, preferably operated under vacuum, such as the one sold by ZZKD Instrument Equipment under the trade name DZF-6010 Vacuum Drying Oven.

It is to be noticed that a programmable dosing pump 11, e.g. a peristaltic pump, is installed between the first container 1 and the second container (doping chamber) 2, in order to feed the at least a second container 2 or doping chamber with the suitable amount necessary to perform the desired doping according to selected and desired parameters. These adjustments are in any case within the skills of the person in the art once the above-mentioned conditions of the doping process are known. Furthermore, the exemplified plant will be equipped with hydraulic connections and relative valves (indicated without reference numbers in FIG. 2) completely conventional in order to guarantee correct operation for the recycling of the culture medium separated from doped graphene and other possible contaminants, for emergency or safety discharge or emptying for periodic washing of the liquids contained in the tanks.

Once the graphene oxide is doped in the second container, the latter is preferably isolated from the recirculation in the system and opened in order to collect the mixture of culture medium, microorganisms and N-S Dual Doped Graphene. After the withdrawal is made, the container is rearranged at the required conditions and can be supplied again with GO (as shown from the reference GO IN of FIG. 2) for a further doping process. According to the needs, it can then be reconnected into the circuit. These operations can be performed thanks to a hydraulic circuit such as that shown in FIG. 2, in which the conduits 20, 60, 70, 80 and the respective valves 21, 61 allow said circulation.

Adjustments of doping conditions are controlled by a suitable computer wherein a program runs in order to receive signals from conventional sensors, probes, thermometers detecting all the working conditions (temperatures, pressures, chemical-physical values such as salinity and pH) and sending command signals to perform a correct management of the doping process in the best way.

In accordance with a further object of this invention, the graphene oxide dually doped with nitrogen and sulfur obtainable according to the above process is characterized by a nitrogen content between 1% and 9%, preferably between 1% and 5%, and a sulfur content between 0.3% and 15%, preferably between 1% and 15%, more preferably between 1% and 10%, referred to the total percentage of atoms inserted in the graphene oxide crystal. These values were obtained in the following way. The chemical analysis adopted is a destructive technique that measures the composition of carbon, sulphur, nitrogen and hydrogen (CHNS) in a sample. The analysis is based on the complete combustion of the sample at about 1000° C. in an oxygen-rich atmosphere (following the method described in: Analytical Methods Committee (2006) Evaluation of analytical instrumentation. Part XIX. CHNS elemental analyzers. *Accreditation and Quality Assurance* 11(11), 569-576. Doi:10.1007/s00769-006-0185-x.), with the collection of gases produced during combustion ($CO_2$, $H_2O$, $N_2$ and $SO_2$), giving the original composition as an elemental percentage. The equipment used for the elemental analysis was LECO CHNS-932 (model NO: 601-800-500), for each measurement about 2 mg of material were used.

It should be noted that, in the case of sulfur, the chemical form in which it is used for doping influences the percentage of the molecule that is incorporated. The percentage of nitrogen and sulfur in N,S-DDG is therefore highly variable and depends on the species used, the chemical form of the precursor (in the case of sulfur) and the growth conditions (in the case of nitrogen) that are used for doping. According to experimental tests carried out, the use of elemental sulphur significantly increases the percentage of its content in graphene oxide.

A particular advantage (besides the cost, the ecological impact and the practicality) of the process according to the present invention would therefore be to be able to regulate the insertion rate of the N and S atoms according to the requirements by varying the conditions specified above. In the case of the present invention, deviations from the optimal S:N ratio (1:1) in favor of sulphur do not adversely affect the catalyzing efficacy of the product, probably because they do not refer exclusively to the sulfur component integrated in the new material. In fact, the addition of a washing phase of doped graphene with organic solvents eliminates surface sulfur deposits and significantly reduces their percentage value.

The results obtained in accordance with the process of this invention show that biologically doped N,S-DDG has excellent oxygen reduction catalysis (ORR) properties (see examples below).

A specific X photoelectron spectroscopy (XPS) analysis was also performed to characterize two samples (AARC-S in the presence of thiosulfate and in the presence of polysulfides) with reference to the chemical forms and bonds of the elements. The technique used made it possible to make an elementary, structural, and quantitative analysis of the surface (some nm depth, typically 2-4 nm) of the samples. The analysis is carried out on solid samples at a vacuum pressure of about 10-8 Pa. The samples are subjected to X-photons ($K_\alpha$ rays of aluminum or alternatively magnesium, in this case aluminum ones were used). The X-photons excite the elements present in the samples and the result can be the direct emission of an electron from a particular energy level (photoionization). The analysis consists in filtering an energy and detecting these photo electrons. The kinetic energy of photoelectrons is a function of the energy of photons X according to the equation:

$$E_{kinetic}(\text{photoelectrons})=E_0(X\text{-rays})-E_{bond}(\text{photoelectrons})$$

The aluminum X-ray source is $K_{\alpha12}=1486.7$ eV. The identification of the elements (qualitative analysis) is done by measuring the binding energy of photoelectrons. The analysis system filters the electrons according to their kinetic energy and the obtained spectra are presented in the binding energy scale (inverse scale). Once the photons are emitted, the element is in an excited state. A possible de-energized state corresponds to the emission of an Auger electron that brings into play three electronic levels. The kinetic energy of the Auger electrons is independent from the energy of the incident X-rays. The X-rays penetrate at an important depth in the sample (one micrometer), but the photoelectrons cannot be extracted from a very thin layer whose thickness is of the order of a few nanometers. The XPS technique is both qualitative and quantitative because the sensitivity is of the order of 0.1% atomic. But the main advantage lies in the possibility to obtain information about the chemical environment of the elements. The precise position in energy of the photoelectron peaks allows to determine the nature of covalent bonds between the analyzed element and its neighbors. In the case of a carbon-oxygen bond, for example, the electronegativity of oxygen will induce a partial transfer of electrons from carbon to oxygen. In this way the carbon protons meet in a less electron-rich environment and the binding energy of these electrons is increased.

In particular, the above analysis was performed with the PHI Versaprobe 500 photoemission spectrometer equipped with a monochromatic X-ray source (aluminum $K_\alpha$ rays), a double anode X-ray source (aluminum and magnesium $K_\alpha$ rays), a charge neutralization system for electrical insulation samples and a hemispherical electronic analyzer. The device also has an electron source (pure Auger analysis with a lateral resolution of about 200 nm), a low-energy ion source (XPS or Auger profilometer) and a cooling system for the sample from the insertion chamber to the analysis chamber. With this equipment it is possible to focus the X-ray source on the sample with a spot diameter ranging from 10 microns to one millimeter. In particular, the analysis on the samples according to the present invention was carried out with an X-ray tube power of 50 W for a circular spot diameter of 200 microns. The information is collected and the average over the whole surface is calculated.

Regarding the spectrophotometer, the photoelectrons are collected at an emergency angle of 45°. The settings are different for spectra and windows. The conditions are dictated by measuring the width at half height (FWHM or Full Width at Half Maximum) of a $3d^{5/2}$ level of silver (acquisition made on the pure silver standard):

Wraith: FWHM=2.3 eV

Windows: FWHM=0.8 eV

The operation was performed using the Multipak logic program. For the quantification, the sensitivity factors method was used, the measurements of the areas are the peaks formed by the windows, after the subtraction of the continuous background with the Shirley method.

The results are represented by Graph A according to FIG. 6 and Table 1 below with reference to the graphene sample doped using the AARC-S strain grown with thiosulfate, while Graph B according to FIG. 6 and Table 2 below refer to the doped sample using the AARC-S strain grown with polysulfides.

13

TABLE 1

| Atoms | C | O | S | N |
|---|---|---|---|---|
| Atoms concentration (%) | 70.2 | 20.7 | 3.1 | 6 |

Uncertainty of measurement 0.5-1%

TABLE 2

| Atoms | C | O | S | N |
|---|---|---|---|---|
| Atoms concentration (%) | 75.1 | 17.6 | 2.3 | 5.0 |

Uncertainty of measurement 0.5-1%

From the above data in the tables the procedure according to the present invention led to a doping with very valid nitrogen and sulfur values. Moreover, the graphs in FIG. 6 show that the doping took place in a deep way, therefore they are not simple depositions. Moreover, comparing the chemical forms of sulfur before and after doping, it can be seen that N,S-DDG is not only doped with sulfur, but also cleaned from surface imperfections (before the process, the only chemical form of sulfur measured corresponds to sulfate, which actually comes from sulfuric acid residues used during the chemical process of isolation of graphene oxide; after the process, sulfur is in a clear minority in the form of sulfate and there is mainly hybridized in 2p form, i.e. inserted in the carbonic hexagon and therefore entirely integrated in the graphene oxide crystal).

Figure 6:
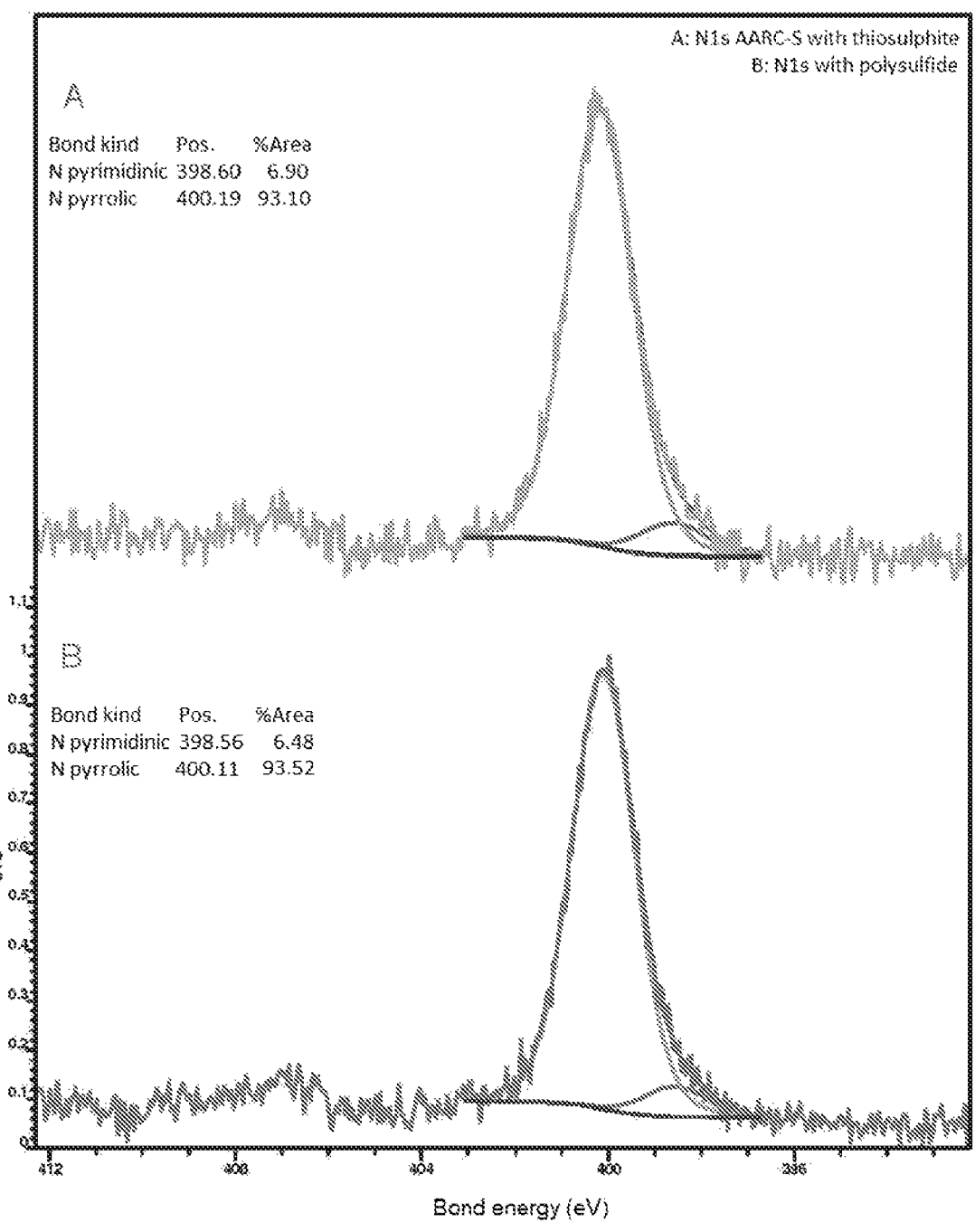
FIG. 6 represents two graphs related to the analysis of the chemical forms of nitrogen in doped graphene samples after treatment with microorganisms of the AARC-S strain cultivated with thiosulphate (graph A) and polysulfides (graph B), respectively.

In particular, with reference to the graphs in FIG. 6, from the value of the bonding energy corresponding to the peak of about 400.1 eV, we get a more precise information that the bond that binds nitrogen to the graphene structure is mainly pyrolytic nitrogen. In practice, compared to the known technique, nitrogen doping is almost exclusively pyrolytic with a value higher than 90% (peak area) than all forms of nitrogen that can be created with doping (pyrimidine, pyrolytic and graphitic). On the contrary, the known technique shows a percentage amount of pyrolytic nitrogen around 40%.

Figure 7:
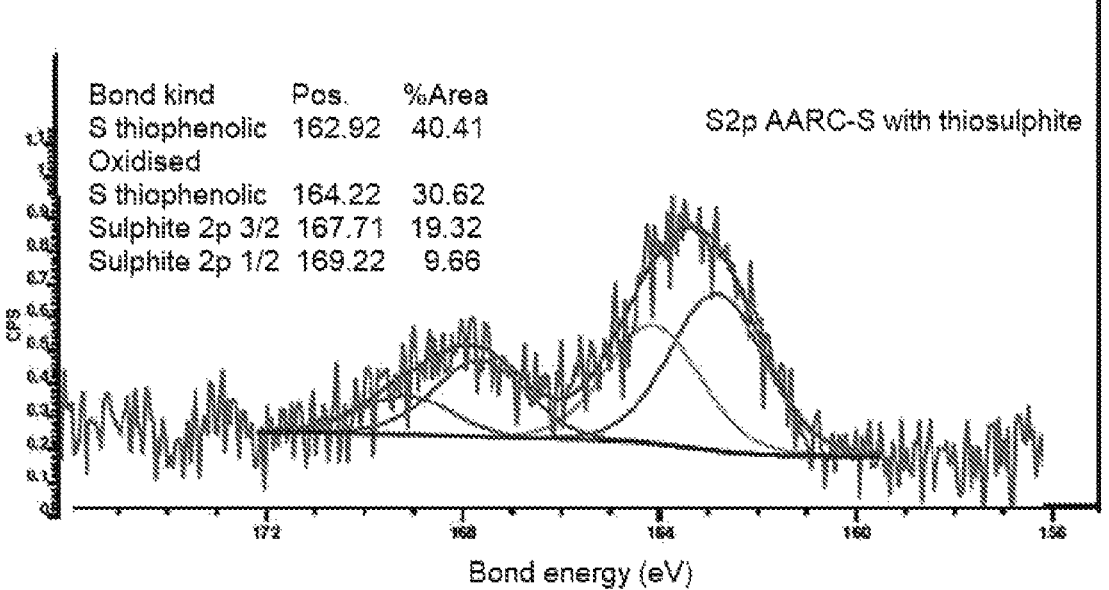
FIG. 7 represents a graph of the XPS spectra of the chemical forms of sulphur in a sample of graphene modified with a microorganism of the invention (AARC-S) grown with thiosulphate.

Similarly, observing the graph of FIG. 7 we can see how the curve that shows a peak of about 162.9 eV indicates the presence of sulfur in the thiophenol form in a percentage greater than 40%. It should be noted that this form of sulfur doping does not appear in any known art.

Consequently, from the above analysis it is evident that the doping process allows to obtain a graphene oxide doped with nitrogen and sulfur characterized by having a percentage of pyrolytic nitrogen greater than 90% and/or a percentage of thiophenol sulfur greater than 40%.

A further object of the invention is therefore the use of doped graphene as previously for the production of electronic and electrochemical components (e.g. fuel cells), analytical systems, purification systems, nanomaterials used as medical, telephone, aeronautical, aerospace, robotics, eco-sustainable macro materials such as automotive mechanical components, aeronautic, aerospace, robotics.

Below are some embodiments of the invention, provided as non-exhaustive examples.

Example 1

Reduction of Graphene Oxide into N,S-DDG by Use of Cell Culture Containing *Natronolimnobius sulfurireducens* (AArc1 Strain Isolated from the Island of Stromboli, Italy)

A 1 L "Schott" bottle was filled with 900 mL of mineral medium containing a 3:1 ratio mixture of the above first and second media (final pH ~9.6) and supplemented with 50 mmoles of polysulfide and 50 mmoles of formate. 100 mL of cell suspension ($10^7$ cells·mL$^{-1}$) were added as inoculum. 1.5 g of graphene oxide powder was subsequently added to initiate the doping process. The headspace of the bottle was then washed 5 times with nitrogen and once with argon and carefully sealed. The culture was kept in stationary mode (without shaking) at 40° C. in thermostat. Each day the bottle was turned upside down to mix the sedimented GO/N,S-DDG. The duration of the GO doping treatment was set at one month. The polysulfide (electron donor in the respiration of said microorganism) is soluble under highly alkaline culture conditions. This also applies to sulfide ions, $CO_2$ molecules (end products of respiration) and format molecules (electron donor in the respiration chain of said microorganism). Therefore, apart from the formed biomass, there are no insoluble products in the culture and dopant medium. The separation of N,S-DDG from biomass was performed after the above one month by centrifugation (4,000×g, 5 min), followed by double washing of the precipitated N,S-DDG with 50 mL isotonic solution (240 g·L$^{-1}$ NaCl) and final filtration on Whatman™ Grade 1 paper filters with a porosity of 8 μm. The resulting material was rinsed through a BIO-PURE® Vacuum filters module composed of a vacuum pump, a filtration ramp, and a filter flask. A hard glass filtration system designed to isolate particles from a liquid suspension was used. Washing was performed two/three times with Milli-Q™ water and then the filtrate was dried for 4 hours at 60° C. in a vacuum oven, type DZF-6010 Vacuum Drying Oven. It must be noted that all N,S-DDG purifications steps do not include any use of organic solvents or acid products.

Figure 3:
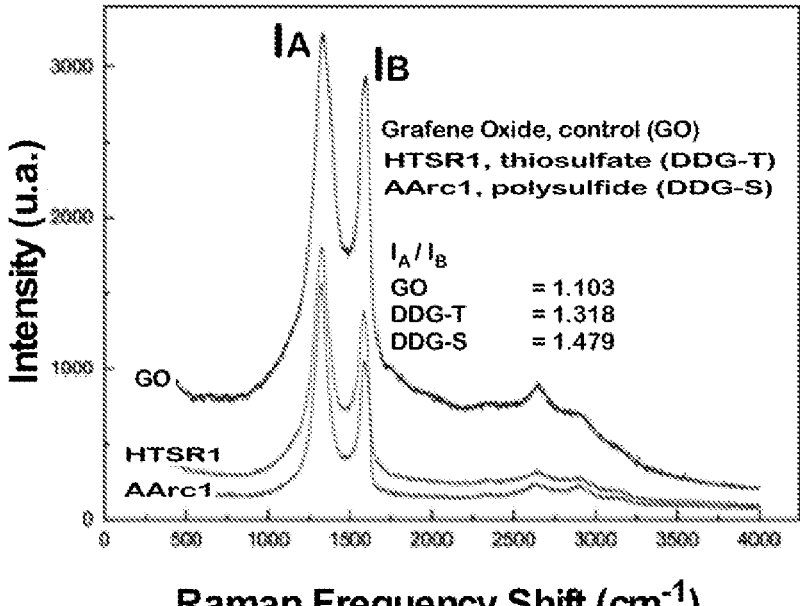
FIG. 3 represents a comparative graph of the result of a Raman spectrometry of graphene oxide (GO) and the graphene oxide reduced in N,S-DDG by the use of different haloarchaea grown on format (electronic donor) when thiosulfate (DDGO-T) and polysulfide (DDGO-S) are supplied as electron acceptors, alternative to elemental sulfur.

The N,S-DDG resulting from the above procedure showed the following characteristics as analyzed by Raman spectrometry. The information obtained in a Raman scattering analysis is graphically represented as a DDG-S diagram (Raman spectrum) in FIG. 3 for N,S-DDG doped according to the present invention (once with HTSR1 in presence of thiosulfate, DDGO-T curve, and a second with AARC1 in presence of polysulfide, DDGO-S curve); where on the abscissae are reported the Raman shifts that correspond to the energies of jumps between the fundamental vibrational levels v=0 and v=1 expressed in cm$^{-1}$ (wave number $\bar{v}=1/\lambda$ remembering the direct proportionality between the energy and the inverse of the wavelength E=hv=hc·1/λ of an electromagnetic radiation). The Raman intensities proportional to the number of Stokes photons collected by the detector of the instrument are reported on the ordinates. Therefore, the N,S-DDG treated as previously, showed the spectrum reported in FIG. 3 obtained with a Renishaw Raman microscope. The monochromatic light is a green laser in the visible spectra (532 nm) with a power of 5 mW. 1.5 mg of sample is required for one measurement. Spectroscopy was performed at 1% power and each measurement was made in a spectrum range of 100-3200 cm$^{-1}$, with each sample accumulating 10 cycles. FIG. 3 shows the significant difference between the spectra of treated and untreated samples. The two peaks characteristic of graphene (A and B, about 1350 cm$^{-1}$ and 1600 cm$^{-1}$ respectively), deduced from similar studies, are presented on each curve. The A-band of the spectra is related to hybridization in the structure, more precisely to the level of disorder usually caused by sp$^2$ hybridization in the structure. The B-band is related to the 'between layers' interactions, typical of multi-layer graphene structure. The Raman bands in the lower frequency ranges (150-550 cm$^{-1}$) give additional evidence to the difference between the treated samples and the GO control sample (GO curve in FIG. 3). They indicate a lower carbon concentration in the treated samples so that reinforcing the postulate that a higher percentage of foreign atoms were inserted. The weaker Raman 2A (2500 cm$^{-1}$) band is also associated with the stratified properties of graphene. The larger the curve 2A, the closer the analyzed material to the uncontaminated graphene structure. Again, the fact that it has a low signal is therefore testifying the excellent quality of the obtained doped graphene. Finally, the ratio between the intensity of the A and B peaks ($I_A/I_B$) is a commonly used parameter to characterize the level of disorder in the crystalline structure of a carbonaceous material. Allowing the evaluation of defective morphology of the analyzed sheets, this parameter provides information on effects of the tested invention (doping) process on the structure of graphene. The higher the $I_A/I_B$ ratio, the higher the doping performance. It has a value of 0.9-1.1 for the GO (control sample) and variable value of 1.2-2.0 (depending on the microorganisms used) for the treated samples. The $I_A/I_B$ ratio of graphene oxide doped by the microorganisms *Natrolimnobius sulfuriducensis* (AArc1) corresponds to about 1.48 (FIG. 3).

Example 2

Reduction of Graphene Oxide in N,S-DDG by Use of Cell Culture Containing *Halodesulfurarchaeum formicicum* (HTSR1 Strain Isolated from the Island of Stromboli, Italy)

A 1 L bottle of Schott was filled with 900 mL of mineral medium containing 240 g·L$^{-1}$ of NaCl, 3 g·L$^{-1}$ of K$_2$HPO$_4$, 0.5 g·L$^{-1}$ of NH$_4$Cl, 1-5 mM of MgCl$_2$×6H$_2$O, 1 ml·L$^{-1}$ of acidic trace metal solution in addition to the following substances (for one liter of culture medium): HCl 0.01 N (i.e. 10 mmol), 0.6 g of CoCl$_2$×6H$_2$O; 30 mg of CuCl$_2$; 0.3 g of FeCl$_2$×4H$_2$O; 1.14 g of H$_3$BO$_3$; 4 g of MnCl$_2$×4H$_2$O; 0.5 g of Na$_2$MoO$_4$×2H$_2$O; 0.3 g of NiCl$_2$×6H$_2$O and finally 0.42 g of ZnCl$_2$. After sterilization, 20-50 mg·L$^{-1}$ of yeast extract, 10 g·L$^{-1}$ of HEPES (final pH ~7.0), 30 mmol of thiosulfate and 50 mmol of formate were added. 100 mL of cell suspension (10$^7$ cells·mL$^{-1}$) were added as inoculum. The headspace of the bottle was washed 5 times with nitrogen and once with argon and carefully sealed. 1.5 g of graphene oxide powder for the doping process was added to a 50 mL flask and the flask was connected to the culture bottle with Norprene tubing with interposition of a peristaltic pump operated at a speed of 40 mL·h$^{-1}$. This pump allows the growing culture to circulate from the bottle into the dopant flask and then return to the culture bottle after passing through a Whatman™ Grade 1 paper filter with 8 μm porosity. As previously made, the culture was performed in stationary mode (without agitation) at 40° C. for one month. In turn, the dopant flask was placed on a Stirrer Pro heating plate/magnetic stirrer regulated with the following parameters: temperature 50° C., stirring at 250 rpm. As before, all products and reagents (obviously omitting GO and produced N, S-DDG) are water soluble. The separation of N,S-DDG from biomass was therefore easily performed by centrifugation (4,000×g, 5 min), followed by two washes with 50 mL of an isotonic solution (240 g·L$^{-1}$) and filtration with Whatman™ Grade 1 paper with 8 μm porosity. The resulting material was then rinsed through the BIO-PURE® Vacuum filters module three times with Milli-Q™ water. It was then dried for 4 hours at 60° C. in a vacuum oven, type DZF-6010 Vacuum Drying Oven.

Again, neither organic solvents nor acids are required for any of the N, S-DDG purification steps.

The N,S-DDG resulting from the above procedure showed the following Raman spectra (DDG-T curve): the area of peak A was 2,692E+05, and the area of peak B was 2,042E+05. To conclude, in EXAMPLE 2, the $I_A/I_B$ ratio of graphene oxide doped by the microorganisms *Halodesulfurarchaeum formicicum* (HTRS1) corresponded to about 1.32 (FIG. 3).

Example 3

Oxygen Reduction Reaction in Electrolytic Cell with N,S-DDG Produced According to Examples 1 and 2

Herein we measured the catalytic performance of graphene, doped according to Examples 1 and 2, for reducing oxygen to hydrogen peroxide.

To obtain the percentage of H$_2$O$_2$ produced, the following measurements for electrochemical characterization were carried out in a three-electrode cell controlled by a bipotentiostat-galvanostat. For this purpose, a rotating ring-disc electrode (RRDE) consisting of a platinum ring and a glassy carbon disc coated with catalytic ink dried on it was used as working electrode. The ORR (Oxygen Reduction Reaction) activity was tested with a polarization curve between 1.1 and 0.2 V vs RHE (Reference Hydrogen Electrode) at 1600 rpm in O$_2$ flow. To detect H$_2$O$_2$ formation, the measurement was performed with the ring electrode held at 1.2 V.

The electrochemical reduction of O$_2$ by a good catalyst (as platinum, known electric conductor) have no intermediate phase and reduce molecular oxygen directly to water (H$_2$O). Hydrogen peroxide is therefore almost completely absent as a by-product of the reaction. Raw graphene oxide, on the other hand, has opposite characteristics: it is an excellent catalyst for the reduction of oxygen into hydrogen peroxide and an inhibitor of hydrogen peroxide reduction in water. Nevertheless, since this raw material does not conduct electricity well, the expected volume of H$_2$O$_2$ produced, although in a majority ratio to water, remains low. The following experiments were performed with electrodes composed of 1 mg of graphene oxide (raw, and doped by HTSR1 and by AArc1 biological activity, respectively).

(i) Using HTSR1-doped graphene oxide samples, we obtain a yield of 92±3% H$_2$O and 8±3% H$_2$O$_2$.

(ii) Using AArc1-doped graphene oxide samples, we obtain a yield of 72±5% H$_2$O and 28±5% H$_2$O$_2$.

(iii) Using HSR2-doped graphene oxide samples, we obtain a yield of 90±2% H$_2$O and 10±2% H$_2$O$_2$.

(iv) Using finally the raw graphene oxide samples, we obtain a yield of 2.4±0.3% H$_2$O and 97.6±3.7% H$_2$O$_2$.

Secondly, the production of hydrogen peroxide (H$_2$O$_2$) produced by electro-synthesis was measured.

(i) HTSR1-doped graphene oxide samples production was evaluated as 4.37 mg·h$^{-1}$ per mg of doped material.

(ii) Aarc1-doped graphene oxide production was evaluated as 32.1 mg·h$^1$ per mg of doped material.

(iii) HSR2-doped graphene oxide production was evaluated as 10.2 mg·h$^1$ per mg of doped material.

(iv) Raw graphene oxide production was evaluated as 10.5 μg·h$^1$ per mg of raw material.

The higher production of H$_2$O$_2$ by the AArc1-modified graphene may be due to the fact that this material is a catalyst slightly less efficient for the reduction of 02 to H$_2$O, this material anyway being electro-conductive. Based on this, it appears that AArc1 modified graphene is a more efficient material to produce H$_2$O$_2$, whereas HSTR1 modified graphene would be more efficient to produce H$_2$O from O$_2$. In any case, the productivity of AArc1 modified graphene and HSTR1 modified graphene are substantially higher than that of the control graphene oxide (respectively 3150 and 970 fold higher, that is three times higher).

Example 4—Cyclic Voltammetry Analysis

The above mentioned electrodes have been modified with different materials: two electrodes with reduced GO once with the above mentioned microorganisms identified with HSR2 code, grown with acetate (curve 2) and with pyruvate (curve 3), once with HSR6 grown with format (curve 4), and once with AArc-S grown with sucrose (curve 5); for all microorganisms elemental sulfur has been used as electron acceptor (FIG. 4A). In FIG. 4B, instead, were used electrodes modified with GO reduced with AArc-1 grown on polysulfide and electrodes with GO reduced with HTSR1, grown on thiosulfate.

All electrodes modified according to this invention exhibit a yield in terms of an enlarged area caused by graphene doped with the process of the invention. This result has demonstrated on the one hand that the doping procedure was correct and on the other hand that it was effective compared to the control represented by the non-doped GO (curve 1) in both graphs. It is to be noticed that although in the graph A the amplitude of the curves area is greater than that of the curves in the graph B, in the case of the graph A, as said, it has been used elemental sulfur as electron acceptor, which involves a washing of the doped graphene with pollutants. On the contrary, in the case of graph B, the acceptors used do not involve the use of pollutants.

Example 5—Photoelectronic X-Ray Spectroscopy

This technique allows the surface characterization of solids by studying the energy of electrons emitted by solids when irradiated with X-ray photons. In this way, you get information about the state of the chemical bonds and the concentration of the atoms on the surface.

The equipment used is the spectrophotometer VG ESCALAB 20CR (VG-Scientific) consisting of a hemispherical electron analyzer, five electron multiplier type detectors (channeltron) and an anode X-ray emission source of Mg ($K_\alpha=1253.6$ eV), with a pressure in the working chamber below 9 Tor and operated at 12 kV and 10 mA. The elements carbon, oxygen, nitrogen and sulfur on the surface of the catalysts, as well as their oxidation states, were analyzed using the XPS technique.

Table 3 below details the values obtained from the atomic surface ratio O/C, N/C and S/C of all catalysts. It can be noted that the treatment of graphene oxide with the halobacteria of the invention results in a reduction of graphene oxide, thus decreasing the surface oxygen and increasing the content of sulfur and nitrogen heteroatoms in samples treated with the bacteria of the invention HTSR.

In particular, the sample treated with HTRS1 has the highest sulfur content, while the sample treated with HSR2 has the highest nitrogen content. Intermediate values of sulfur, nitrogen and oxygen are obtained with the sample treated with HSR6.

TABLE 3

|  | Bond S/C | Bond N/C | Bond O/C |
| --- | --- | --- | --- |
| HTRS1 | 0.07 | 0.06 | 0.27 |
| HSR6 | 0.05 | 0.07 | 0.23 |

TABLE 3-continued

|  | Bond S/C | Bond N/C | Bond O/C |
| --- | --- | --- | --- |
| HSR2 | 0.03 | 0.09 | 0.25 |
| Graphene Oxide | 0.009 | 0.01 | 0.55 |

In addition, it should be noted that the O/C ratios of three samples treated with the microorganisms of the invention correspond to less than half of the graphene oxide one. This means that the electronic conductivity is more than duplicated in these samples.

FIG. 5 shows the XPS spectra of hybridization of three different elements A) carbon 1s, B) nitrogen 1s and C) sulphur 2p, obtained from three samples after treatment with HSR2, HSR6 and HTRS1, respectively, against an untreated graphene oxide sample.

The spectra A) show the C1s zone of all the samples, outlining their distribution in 4 subgroups that correspond to the graphite, hydroxyl, epoxy and carboxylic oxidation states, respectively. The subgroup with binding energy lower than ~284.53 eV corresponds to the graphite carbon (C—C), while the subsequent subgroups correspond to higher oxidation states with higher binding energies. The largest difference between graphene oxide and samples treated with HSR microorganisms is indicated by the amplitude of the curve for the oxidized carbon subgroup (C=O at 287.66 eV and C—O, C—O—C, C—O at 286.55 eV). In the treated samples, it is significantly lower than in graphene oxide. This shows that there has been a significant reduction in graphene oxide in the presence of microorganisms.

The spectra of energy level N1s (in FIG. 5 B) were equally divided into three peaks. The lowest binding energy peak (~399 eV) corresponds to pyrimidine nitrogen, followed by pyrolytic nitrogen at ~400 eV and graphite nitrogen at ~402 eV. The peak with the highest intensity is pyrimidine nitrogen in all 3 samples treated. The observed components are similar in all three samples except for HSR2 where the proportion of N-pyrrolic nitrogen is slightly higher.

The S2p energy level spectra in FIG. 5 C) for HTSR samples were divided into four components, except for the graphene oxide sample which was kept under a single group. As for nitrogen, the S2p signal is very low for Graphene Oxide. The peaks obtained in the HSR samples around ~163-164 eV and ~166 eV are due to the sulphur in the aromatic chains of graphene, thiophene and oxidized thiophene (C—SO, C—SO$_2$), respectively. Instead, a higher state of oxidation of sulphur in the form of disulfate (SO$_4^{2-}$), sulfite (SO$_3^{2-}$) or thiosulfite (S$_2$O$_3^{2-}$—) would correspond to binding energies greater than 167 eV.

The graphs, therefore, demonstrate an excellent performance in the reduction of graphene when treated with the bacteria of the present invention, as well as an increase in the content of hetero-atoms N and S on the surface of the graphene even compared to similar processes based on the use of other microorganisms, in particular with specific forms such as pyrrolic nitrogen and thiophenic sulfur.

The invention claimed is:

1. A process for producing graphene doped with nitrogen and sulfur atoms (N,S-DDG) comprising:
   providing microorganisms of a Halobacteria class which are strictly anaerobic and sulfite-reducing and that lives between 20° C. and 50° C. in salinity condition over 200 g·L-1 and at a pH comprised between 7.0 and 10.0;
   culturing the microorganisms in a medium comprising an electronic donor in an amount up to 100 mmol hydrogen ($H_2$), acetate ($C_2H_4O_2$), formate ($CH_2O_2$), glycerol ($C_3H_8O_5$), glucose ($C_6H_{12}O_6$), sucrose ($C_{12}H_{22}O_{11}$) and other similar sugars, lactate ($C_3H_6O_3$), short chain fatty acids ($C_4$-$C_9$) and/or pyruvate ($C_3H_4O_3$), and as an electronic acceptor in an amount up to 50 mmol a sulfur form more oxidized than $S^{2-}$ comprising elemental sulfur ($S_8°$), polysulfide (—S—$S_6$—S—), thiosulfate ($S_2O_3^{2-}$), dimethylsulfoxide ($CH_3)_2SO$, and/or tetrathionate ($S_4O_6^{2-}$);

contacting a solution of graphene oxide (GO) with a culturing medium containing the microorganisms for a time sufficient to obtain the doping with nitrogen and sulfur; and washing the graphene to eliminate both an organic phase and molecules containing nitrogen and sulfur that have not reacted with graphene oxidized.

2. The process of claim 1, wherein said microorganisms are selected from the genus *Halalkaliarchaeum, Halanaeroarchaeum, Halodesulfurarchaeum, Halarchaeoglobus Natranaeroarchaeum* and *Natronolimnobius*.

3. The process of claim 1, wherein the culturing medium comprises 240 g·$L^{-1}$ of NaCl, 3 g·$L^{-1}$ of $K_2HPO_4$, 0.5 g·$L^{-1}$ of $NH_4Cl$, and 1-5 mM of $MgCl_2 \times 6H_2O$, is sterilized and added with 20-50 mg·$L^{-1}$ of yeast extract, 1 ml·$L^{-1}$ of acid trace metal solution, 1 mL·$L^{-1}$ of selenium/tungsten alkaline solution and a vitamin mix.

4. The process of claim 3, wherein the acid trace metal solution comprises the following substances (for liter of culture medium): HCl 0.01 N, 0.6 g of $CoCl_2 \times 6H_2O$, 30 mg of $CuCl_2$, 0.3 g of $FeCl_2 \times 4H_2O$, 1.14 g of $H_3BO_3$, 4 g of $MnCl_2 \times 4H_2O$, 0.5 g of $Na_2MoO_4 \times 2H_2O$, 0.3 g of $NiCl_2 \times 6H_2O$ and 0.42 g of $ZnCl_2$, the vitamin mix comprising per 1 L of deionized water: 1 mg of $B_{12}$ vitamin, 20 mg of biotin, 20 mg of folic acid, 50 mg of nicotinic acid, 50 mg of p-aminobenzoic acid, 50 mg pantothenate calcium, 100 mg of pyridoxine×HCl, 50 mg of riboflavin, 50 mg of thiamine and 50 mg of thioctic acid and, the selenium/tungsten alkaline solution is composed of the following substances (for liter of 0.01 N NaOH): 2 mg of $Na_2SeO_3$ and 4 mg of $Na_2WO_4 \times 1.5H_2O$.

5. The process of claim 3, wherein the culture medium further comprises 10 g·$L^{-1}$ of HEPES.

6. The process of claim 1, wherein the culture medium is a mixture of two culture medium: the first one comprising 240 g·$L^{-1}$ of NaCl, 5 g·$L^{-1}$ of KCl, 2 g·$L^{-1}$ of $K_2HPO_4$; 0.5 g·$L^{-1}$ of $NH_4Cl$, the second 190 g·$L^{-1}$ of $Na_2CO_3$, 30 g·$L^{-1}$ of $NaHCO_3$, 16 g·$L^{-1}$ of NaCl, 5.0 g·$L^{-1}$ of KCl, 8 mM of $NH_4Cl$, 1.0 g·$L^{-1}$ of $K_2HPO_4$, and both the culture medium being added with 1 mM of $MgCl_2 \times 6H_2O$, 1 mL·$L^{-1}$ of acid trace metal solution, a vitamin mix, 1 mL·$L^{-1}$ of alkaline solution selenium/tungsten e 20 mg·$L^{-1}$ of yeast extract.

7. The process of claim 1, wherein the contacting graphene oxide (GO) with the cell culture is carried out contacting the graphene oxide in the form of a powder at a concentration up to 2 mg·$mL^{-1}$, for a time comprised between 10 days and 30 days at a temperature between 20° C. and 50° C., with or without stirring.

8. The process of claim 1, wherein the washing the graphene comprises a separation of organic material from graphene oxide by centrifugation and/or/filtration, followed by washing with isotonic solution and filtration with glass fibre filters with pore diameter of 5-20 µm, the washing being carried out with purified water and repeated two or more times, and a final step of drying is carried out for 2-6 hours at 40°-80° C.

9. A graphene oxide doped with nitrogen and sulfur made by the process of claim 1, comprising nitrogen atoms, as percentage on the total percentage of atoms, between 1% and 9%, and sulfur atoms between 0.3% and 15%.

10. The graphene oxide of claim 9, wherein nitrogen is in a pyloric form in a percentage higher that 90% and/or sulfur is in a thiophenolic form in a percentage higher that 40%.

\* \* \* \* \*